United States Patent [19]

Nakamura et al.

[11] Patent Number: 4,794,183

[45] Date of Patent: Dec. 27, 1988

[54] CERTAIN TETRAHYDRO-FURAN OR PYRAN PHOSPHATE-ETHYLENE OR PROPYLENE AMMONIUM DERIVATIVES

[75] Inventors: Norio Nakamura; Hideki Miyazaki; Fusaaki Shimizu; Kazuhiko Sasagawa, all of Hiromachi, Japan

[73] Assignee: Sankyo Company Limited, Tokyo, Japan

[21] Appl. No.: 818,876

[22] Filed: Jan. 14, 1986

[30] Foreign Application Priority Data

Jan. 16, 1985 [JP] Japan .................................. 60-4054

[51] Int. Cl.$^4$ ........................... C07F 9/58; C07F 9/141
[52] U.S. Cl. .................................. 546/22; 546/23; 548/112; 544/157; 544/232; 540/542; 549/222; 514/89
[58] Field of Search ................. 546/22, 23; 549/218, 549/222; 514/89, 99, 92

[56] References Cited

U.S. PATENT DOCUMENTS 4,749,696 6/1988 Lee .......................... 514/89

*Primary Examiner*—Alan L. Rotman
*Attorney, Agent, or Firm*—Frishauf, Holtz, Goodman & Woodward

[57] ABSTRACT

Compounds of formula (I):

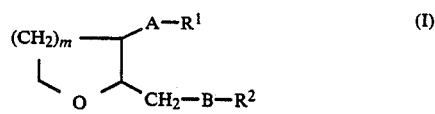

[wherein: m is 1–3; A and B are oxygen or sulfur; and one of $R^1$ and $R^2$ is $C_{10}$–$C_{22}$ alkyl and the other is a group of formula (II).

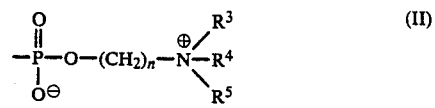

where: n is 2 or 3; and $-NR^3R^4R^5$ is an amino group] and salts thereof are effective anti-cancer agents.

14 Claims, No Drawings

CERTAIN TETRAHYDRO-FURAN OR PYRAN PHOSPHATE-ETHYLENE OR PROPYLENE AMMONIUM DERIVATIVES

BACKGROUND OF THE INVENTION

The present invention relates to a series of novel phosphate ester derivatives containing a cyclic ether system and provides processes for producing these compounds and compositions containing them for use as anti-cancer agents.

Many compounds have been shown to have anti-tumor activity, but the number of compounds available for practical, therapeutic use is relatively small. The problem is that the majority of compounds which have therapeutic effects against tumor cells are also toxic to normal tissues for various reasons. For example, it is known that 3-O-alkyl lysoglycerophospholipid derivatives shown an anti-cancer effect and, e.g., UK Patent Specification No. 1,583,661 discloses a compound of formula:

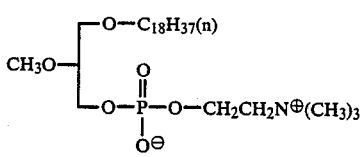

However, compounds of this type have an activity similar to that of platelet activating factor (hereinafter abbreviated to "PAF"), for example platelet-aggregation and hypotensive activities. These unwanted activities render the 3-O-alkyl lysoglycerophospholipid derivatives extremely toxic.

European Patent Publication No. 103,877 discloses a series of phosphate derivatives which are said to have anti-tumor activity, but these are derivatives of sugars, which are conceptually and structurally very different from the compounds of the present invention.

BRIEF SUMMARY OF INVENTION

The present invention provides a series of new phosphate ester derivatives containing a cyclic ether group, which derivatives have shown anti-tumor activity, in various kinds of experimental tumor systems. Moreover, because these derivatives appear to be free from PAF-like activity, they have a very low toxicity and can, therefore, if necessary be employed in relatively high dosages.

The compounds of the invention are compounds of formula (I):

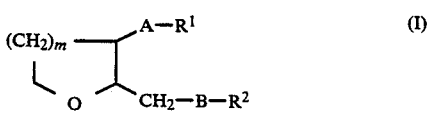

in which:

m is an integer of from 1 to 3;

A and B are independently selected from the group consisting of oxygen atoms and sulfur atoms; and one of $R^1$ and $R^2$ represents a $C_{10}$–$C_{22}$ alkyl group and the other represents a group of formula (II):

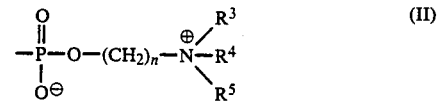

in which:

n represents an integer of from 2 to 3;

$R^3$, $R^4$ and $R^5$ are independently selected from the group consisting of hydrogen atoms and $C_1$–$C_6$ alkyl groups, or $R^3$ and $R^4$ or $R^3$, $R^4$ and $R^5$, together with the nitrogen atom to which they are attached, form a heterocyclic ring which may be aromatic or partly or wholly saturated;

and pharmaceutically acceptable salts thereof.

The compounds of the invention may be prepared by reacting a compound of formula (III):

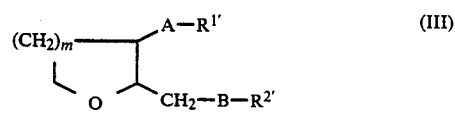

(in which m, A and B are as defined above; and one of $R^{1'}$ and $R^{2'}$ represents a $C_{10}$–$C_{22}$ alkyl group and the other represents a group of formula (IV):

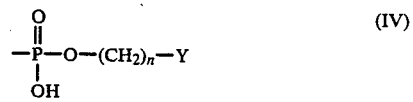

(in which n is as defined and Y represents a halogen atom) or a group of formula (V):

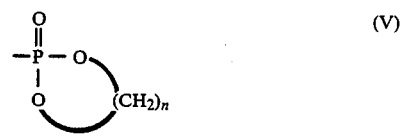

(in which n is as defined above) with an amine compound of formula (VI):

$$R^3NR^4R^5 \qquad (VI)$$

DETAILED DESCRIPTION OF INVENTION

The compounds of the invention can exist in the form of an intramolecular salt, i.e. as shown above in which one of $R^1$ and $R^2$ represents a group of formula (II):

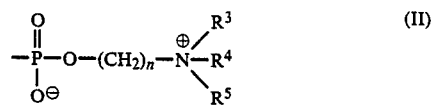

(in which n, $R^3$, $R^4$ and $R^5$ are as defined above) or it may exist in the form of a salt, in which one of $R^1$ and $R^2$ represents a group of formula (IIa):

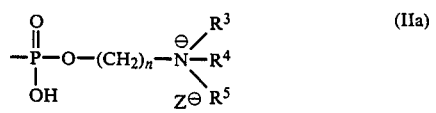

(in which n, $R^3$, $R^4$ and $R^5$ are as defined above, and Z represents a pharmaceutically acceptable anion, preferably a hydroxy group, a halogen atom, a $C_1$-$C_6$ alkylsulfonyloxy group or an arylsulfonyloxy group).

Salts in which one of $R^1$ and $R^2$ represents the aforementioned group of formula (IIa) can also form salts with cations, particularly metals (e.g. alkali metals such as sodium or potassium or alkaline earth metals such as calcium or magnesium), in which the cation replaces the hydrogen atom of the hydroxy group attached to the phosphorus atom in the group of formula (IIa).

Where Z in the above formula (IIa) represents a halogen atom, this may be, for example, a chlorine, bromine or iodine atom. Where Z represents an alkylsulfonyloxy group, the alkyl part is $C_1$-$C_6$ and may be a straight or branched chain group; examples include the methanesulfonyloxy and ethanesulfonyloxy groups. Where Z represents an arylsulfonyloxy group, the aryl part is a $C_6$-$C_{10}$ carbocyclic aryl group, which may be substituted or unsubstituted and, if substituted, may have from 1 to 3 substituents preferably selected from the group consisting of $C_1$-$C_4$ alkyl (preferably methyl) groups, halogen atoms, $C_1$-$C_4$ alkoxy groups and nitro groups. Examples of such arylsulfonyloxy groups include the benzenesulfonyloxy and p-toluenesulfonyloxy groups.

In the compounds of the invention, one of $R^1$ and $R^2$ represents the above defined group of formula (II) [or (IIa)], whilst the other represents a $C_{10}$-$C_{22}$ alkyl group, which may be a straight or branched chain group. Examples of such groups include the decyl, 3-methylnonyl, 8-methylnonyl, 3-ethyloctyl, 3,7-dimethyloctyl, undecyl, dodecyl, tridecyl, tetradecyl, pentadecyl, hexadecyl, 1-methylpentadecyl, 14-methylpentadecyl, 13,13-dimethyltetradecyl, heptadecyl, 15-methylhexadecyl, octadecyl, 1-methylheptadecyl, nonadecyl, icosyl, henicosyl and docosyl groups. Straight and branched chain alkyl groups having from 16 to 18 carbon atoms, for example the hexadecyl, 1-methylpentadecyl, 14-methylpentadecyl, 13,13-dimethyltetradecyl, heptadecyl, 15-methylhexadecyl, octadecyl and 1-methylheptadecyl groups are preferred.

Where $R^3$, $R^4$ or $R^5$ represents an alkyl group, this is a lower alkyl group having from 1 to 6 carbon atoms and it may be a straight or branched chain group. The group more preferably has from 1 to 5 carbon atoms and examples of such groups include the methyl, ethyl, propyl, isopropyl, butyl, isobutyl, sec-butyl, t-butyl and pentyl groups, of which the methyl and ethyl groups are preferred.

Where one of $R^3$, $R^4$ and $R^5$ (for example $R^5$) represents a hydrogen atom, the group of formula (II) which is represented by one of $R^1$ and $R^2$ may be represented by the following formula (IIb):

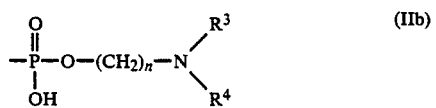

(IIb)

(in which $R^3$, $R^4$ and n are as defined above) which is tautomeric with the group of formula (IIc):

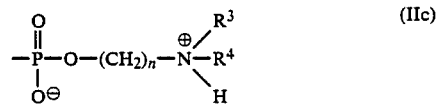

(IIc)

(in which $R^3$, $R^4$ and n are as defined above).

Where $R^3$ and $R^4$, together with the nitrogen atom to which they are attached, form a heterocyclic ring system, this is necessarily a non-aromatic ring system and should contain from 5 to 7 ring atoms (including the aforementioned nitrogen atom) and have at least one hetero-atom (the aforementioned nitrogen atom) and may have additionally from 0 to 3 hetero-atoms selected from the group consisting of nitrogen, oxygen and sulfur atoms. Examples of such non-aromatic heterocyclic groups include the 1-pyrrolidinyl, piperidino, 1-azepinyl, morpholino and thiomorpholino (=perhydro-1,4-thiazin-4-yl) groups. Of these, the piperidino group is preferred. These non-aromatic heterocyclic groups may be substituted or unsubstituted and, if substituted, the substituents may be selected from those defined below in relation to aromatic heterocyclic groups. However, the non-aromatic heterocyclic groups are preferably unsubstituted.

Where $R^3$, $R^4$ and $R^5$, together with the nitrogen atom to which they are attached, form a heterocyclic ring, this is preferably an aromatic heterocyclic ring, and preferably has from 5 to 10 ring atoms, of which at least the aforementioned nitrogen atom is a hetero-atom and which may contain from 0 to 3 additional hetero-atoms selected from the group consisting of nitrogen, oxygen and sulfur atoms. Examples of such aromatic heterocyclic rings include the 1-pyridyl, 3-thiazolyl, 3-oxazolyl, 1-pyridazinyl, 1-quinolyl, 2-isoquinolyl, 1-imidazolyl and N-triazolyl groups. Such groups may be substituted or unsubstituted and, if substituted, may have at least one (and preferably from 1 to 3) substituents selected from the group consisting of $C_1$-$C_6$ alkyl groups (such as those exemplified above in relation to $R^3$, $R^4$ and $R^5$), $C_1$-$C_6$ alkoxy groups (such as the methoxy, ethoxy, propoxy, isopropoxy, butoxy and isobutoxy groups, preferably the methoxy or ethoxy groups), carbamoyl groups and halogen atoms (such as the fluorine, chlorine or bromine atoms). Of these, the unsubstituted 1-pyridyl and 3-thiazolyl groups are preferred.

Since the carbon atoms at the α- and β-positions (relative to the ether oxygen atom) of the ether ring are asymmetric, a total of at least four stereoisomers of each compound is possible, in which each asymmetric carbon atom is in the R-configuration or the S-configuration, i.e. R,R, R,S, S,S and S,R isomers. The present invention envisages both the individual isolated isomers, as well as mixtures of these isomers. Where the process of the invention produces the compounds of the invention in the form of mixtures of isomers, these may, if desired, be employed as the mixtures or the mixtures may be separated into individual isomers by conventional separation or resolution techniques.

Of the compounds of the invention, we prefer those compounds in which:
(1) m is 1 or 2.
(2) A and B both represent oxygen atoms.
(3) n is 2.
(4) $R^3$, $R^4$ and $R^5$ are all $C_1$-$C_6$ alkyl groups, or $R^3$, $R^4$ and $R^5$ together with the nitrogen atom to which they are attached represent a 1-pyridyl group, or $R^3$ and $R^4$ together with the nitrogen atom to which they are attached represent a piperidino group and $R^5$ represents a hydrogen atom or a $C_1$-$C_6$ alkyl group.

(5) The groups represented by —A—$R^1$ and —CH$_2$—B—$R^2$ are in the trans configuration.

(6) One of $R^1$ and $R^2$ represents an alkyl group having from 16 to 18 carbon atoms;

m is 1 or 2;

A and B both represent oxygen atoms;

n is 2;

$R^3$, $R^4$ and $R^5$ all represent $C_1$-$C_6$ alkyl groups, or $R^3$, $R^4$ and $R^5$ together with the nitrogen atom to which they are attached represent a 1-pyridyl group, or $R^3$ and $R^4$ together with the nitrogen atom to which they are attached represent a piperidino group and $R^5$ represents a hydrogen atom or a $C_1$-$C_6$ alkyl group; and the groups represented by —A—$R^1$ and —CH$_2$—B—$R^2$ are in the trans configuration.

Examples of certain preferred compounds of the present invention are given in the following Tables 1-6.

In the following Tables, the abbreviations used have the meanings:

| | |
|---|---|
| Me | methyl |
| Pip+ | piperidinium |
| Pyr+ | pyridinium |
| Thi+ | 1,3-thiazolium |

All alkyl groups are "normal", i.e. straight chain, except where explicitly shown otherwise.

Compounds of formula (I-1):

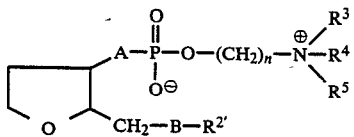

are as defined in Table 1.

TABLE 1

| Cpd No | A | B | $R^{2'}$ | n | —N+$R^3R^4R^5$ |
|---|---|---|---|---|---|
| 1 | O | O | $C_{14}H_{29}CH(Me)$— | 2 | —N+$H_3$ |
| 2 | O | O | $Me_3C$—$(CH_2)_{12}$— | 2 | —N+$Me_3$ |
| 3 | O | O | $C_{16}H_{33}$— | 2 | Thi+ |
| 4 | O | O | $Me_2CH$—$(CH_2)_{13}$— | 2 | 1-Me—Pip+ |
| 5 | O | O | $C_{16}H_{33}$— | 2 | —N+$HMe_2$ |
| 6 | O | O | $C_{16}H_{33}$— | 2 | —N+$Me_3$ |
| 7 | O | O | $C_{16}H_{33}$— | 2 | Pyr+ |
| 8 | O | O | $C_{16}H_{33}$— | 2 | 1-Me—Pip+ |
| 9 | O | O | $C_{16}H_{33}$— | 3 | —N+$H_3$ |
| 10 | O | O | $C_{16}H_{33}$— | 3 | —N+$Me_3$ |
| 11 | O | O | $C_{16}H_{33}$— | 3 | Pyr+ |
| 12 | O | O | $C_{16}H_{33}$— | 3 | 1-Me—Pip+ |
| 13 | O | O | $Me_2CH$—$(CH_2)_{15}$— | 2 | —N+$HMe_2$ |
| 14 | O | O | $C_{14}H_{29}CH(Me)$— | 2 | —N+$Me_3$ |
| 15 | O | O | $Me_3C$—$(CH_2)_{14}$— | 2 | Pyr+ |
| 16 | O | O | $C_{18}H_{37}$— | 2 | Thi+ |
| 17 | O | O | $C_{18}H_{37}$— | 2 | —N+$H_3$ |
| 18 | O | O | $C_{18}H_{37}$— | 2 | —N+$Me_3$ |
| 19 | O | O | $C_{18}H_{37}$— | 2 | Pyr+ |
| 20 | O | O | $C_{18}H_{37}$— | 2 | 1-Me—Pip+ |
| 21 | O | O | $C_{18}H_{37}$— | 3 | —N+$H_3$ |
| 22 | O | O | $C_{18}H_{37}$— | 3 | —N+$Me_3$ |
| 23 | O | O | $C_{18}H_{37}$— | 3 | Pyr+ |
| 24 | O | O | $C_{18}H_{37}$— | 3 | 1-Me—Pip+ |
| 25 | O | S | $C_{16}H_{33}$— | 2 | —N+$HMe_2$ |
| 26 | O | S | $C_{16}H_{33}$— | 2 | —N+$Me_3$ |
| 27 | O | S | $C_{16}H_{33}$— | 2 | Pyr+ |
| 28 | O | S | $C_{16}H_{33}$— | 2 | 1-Me—Pip+ |
| 29 | O | S | $C_{18}H_{37}$— | 2 | —N+$H_3$ |

TABLE 1-continued

| Cpd No | A | B | $R^{2'}$ | n | —N+$R^3R^4R^5$ |
|---|---|---|---|---|---|
| 30 | O | S | $C_{18}H_{37}$— | 2 | —N+$Me_3$ |
| 31 | O | S | $C_{18}H_{37}$— | 2 | Pyr+ |
| 32 | O | S | $C_{18}H_{37}$— | 2 | 1-Me—Pip+ |
| 33 | S | O | $C_{16}H_{33}$— | 2 | —N+$H_3$ |
| 34 | S | O | $C_{16}H_{33}$— | 2 | —N+$Me_3$ |
| 35 | S | O | $C_{16}H_{33}$— | 2 | Pyr+ |
| 36 | S | O | $C_{16}H_{33}$— | 2 | Thi+ |
| 37 | S | O | $C_{18}H_{37}$— | 2 | —N+$HMe_2$ |
| 38 | S | O | $C_{18}H_{37}$— | 2 | —N+$Me_3$ |
| 39 | S | O | $C_{18}H_{37}$— | 2 | Pyr+ |
| 40 | S | O | $C_{18}H_{37}$— | 2 | 1-Me—Pip+ |
| 41 | S | S | $C_{16}H_{33}$— | 2 | —N+$H_3$ |
| 42 | S | S | $C_{16}H_{33}$— | 2 | —N+$Me_3$ |
| 43 | S | S | $C_{16}H_{33}$— | 2 | Pyr+ |
| 44 | S | S | $C_{16}H_{33}$— | 2 | —N+$HMe_2$ |
| 45 | S | S | $C_{18}H_{37}$— | 2 | —N+$H_3$ |
| 46 | S | S | $C_{18}H_{37}$— | 2 | —N+$Me_3$ |
| 47 | S | S | $C_{18}H_{37}$— | 2 | Pyr+ |
| 48 | S | S | $C_{18}H_{37}$— | 2 | 1-Me—Pip+ |

Compounds of formula (I-2):

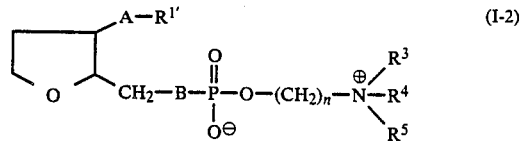

are as defined in Table 2.

TABLE 2

| Cpd No | A | B | $R^{1'}$ | n | —N+$R^3R^4R^5$ |
|---|---|---|---|---|---|
| 49 | O | O | $C_{14}H_{29}$—CH(Me)— | 2 | —N+$H_3$ |
| 50 | O | O | $Me_3C$—$(CH_2)_{12}$— | 2 | —N+$Me_3$ |
| 51 | O | O | $C_{16}H_{33}$ | 2 | Thi+ |
| 52 | O | O | $Me_2CH$—$(CH_2)_{13}$— | 2 | —N+$HMe_2$ |
| 53 | O | O | $C_{16}H_{33}$— | 2 | —N+$Me_3$ |
| 54 | O | O | $C_{16}H_{33}$— | 2 | Pyr+ |
| 55 | O | O | $C_{16}H_{33}$— | 3 | —N+$Me_3$ |
| 56 | O | O | $C_{16}H_{33}$— | 3 | 1-Me—Pip+ |
| 57 | O | O | $C_{18}H_{37}$— | 2 | —N+$H_3$ |
| 58 | O | O | $C_{18}H_{37}$— | 2 | Pyr+ |
| 59 | O | O | $C_{18}H_{37}$— | 2 | —N+$Me_3$ |
| 60 | O | O | $C_{18}H_{37}$— | 2 | 1-Me—Pip+ |
| 61 | O | O | $C_{18}H_{37}$— | 3 | —N+$Me_3$ |
| 62 | O | O | $C_{18}H_{37}$— | 3 | Pyr+ |
| 63 | O | S | $C_{16}H_{33}$— | 2 | —N+$Me_3$ |
| 64 | O | S | $C_{18}H_{37}$— | 2 | —N+$Me_3$ |
| 65 | S | O | $C_{16}H_{33}$— | 2 | —N+$Me_3$ |
| 66 | S | O | $C_{18}H_{37}$— | 2 | —N+$Me_3$ |
| 67 | S | S | $C_{16}H_{33}$— | 2 | —N+$Me_3$ |
| 68 | S | S | $C_{18}H_{37}$— | 2 | —N+$Me_3$ |

Compounds of formula (I-3):

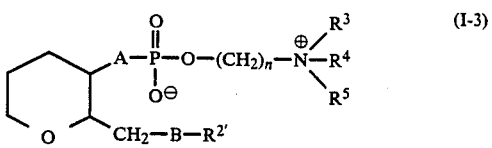

are as defined in Table 3.

TABLE 3

| Cpd No | A | B | $R^{2'}$ | n | —N+$R^3R^4R^5$ |
|---|---|---|---|---|---|
| 69 | O | O | $C_{16}H_{33}$— | 2 | —N+$Me_3$ |
| 70 | O | O | $C_{16}H_{33}$— | 2 | Pyr+ |
| 71 | O | O | $C_{18}H_{37}$— | 2 | —N+$Me_3$ |

TABLE 3-continued

| Cpd No | A | B | $R^{2'}$ | n | $-N^+R^3R^4R^5$ |
|---|---|---|---|---|---|
| 72 | O | O | $C_{18}H_{37}-$ | 2 | $Pyr^+$ |
| 73 | O | S | $C_{16}H_{33}-$ | 2 | $-N^+Me_3$ |
| 74 | O | S | $C_{18}H_{37}-$ | 2 | $-N^+HMe_2$ |
| 75 | S | O | $C_{16}H_{33}-$ | 2 | $-N^+Me_3$ |
| 76 | S | O | $C_{18}H_{37}-$ | 2 | $-N^+Me_3$ |
| 77 | S | S | $C_{16}H_{33}-$ | 2 | $-N^+Me_3$ |
| 78 | S | S | $C_{18}H_{37}-$ | 2 | $-N^+Me_3$ |

Compounds of formula (I-4):

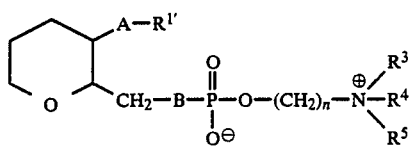
(I-4)

are as defined in Table 4.

TABLE 4

| Cpd No | A | B | $R^{1'}$ | n | $-N^+R^3R^4R^5$ |
|---|---|---|---|---|---|
| 79 | O | O | $C_{16}H_{33}-$ | 2 | $-N^+Me_3$ |
| 80 | O | O | $C_{16}H_{33}-$ | 2 | $1\text{-Me}-Pip^+$ |
| 81 | O | O | $C_{18}H_{37}-$ | 2 | $-N^+Me_3$ |
| 82 | O | O | $C_{18}H_{37}-$ | 2 | $Thi^+$ |
| 83 | O | S | $C_{16}H_{33}-$ | 2 | $-N^+Me_3$ |
| 84 | O | S | $C_{18}H_{37}-$ | 2 | $-N^+HMe_2$ |
| 85 | S | O | $C_{16}H_{33}-$ | 2 | $-N^+Me_3$ |
| 86 | S | O | $C_{18}H_{37}-$ | 2 | $-N^+Me_3$ |
| 87 | S | S | $C_{16}H_{33}-$ | 2 | $-N^+Me_3$ |
| 88 | S | S | $C_{18}H_{37}-$ | 2 | $-N^+Me_3$ |

Compounds of formula (I-5):

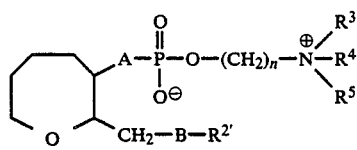
(I-5)

are as defined in Table 5.

TABLE 5

| Cpd No | A | B | $R^{2'}$ | n | $-N^+R^3R^4R^5$ |
|---|---|---|---|---|---|
| 89 | O | O | $C_{16}H_{33}-$ | 2 | $-N^+Me_3$ |
| 90 | O | O | $C_{18}H_{37}-$ | 2 | $-N^+Me_3$ |
| 91 | O | S | $C_{16}H_{33}-$ | 2 | $-N^+Me_3$ |
| 92 | S | O | $C_{18}H_{37}-$ | 2 | $-N^+HMe_2$ |
| 93 | S | S | $C_{16}H_{33}-$ | 2 | $-N^+Me_3$ |

Compounds of formula (I-6):

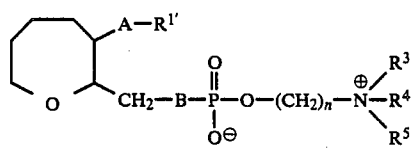
(I-6)

are as defined in Table 6.

TABLE 6

| Cpd No | A | B | $R^{1'}$ | n | $-N^+R^3R^4R^5$ |
|---|---|---|---|---|---|
| 94 | O | O | $C_{16}H_{33}-$ | 2 | $-N^+Me_3$ |

TABLE 6-continued

| Cpd No | A | B | $R^{1'}$ | n | $-N^+R^3R^4R^5$ |
|---|---|---|---|---|---|
| 95 | O | O | $C_{18}H_{37}-$ | 2 | $-N^+Me_3$ |
| 96 | O | S | $C_{16}H_{33}-$ | 2 | $-N^+Me_3$ |
| 97 | S | O | $C_{18}H_{37}-$ | 2 | $-N^+HMe_2$ |
| 98 | S | S | $C_{16}H_{33}-$ | 2 | $-N^+Me_3$ |

Because of the presence of asymmetric carbon atoms at α- and β-positions (relative to the ether oxygen atom in the ether ring) the compounds of the invention can exist, as explained previously, as four different stereoisomers. Specific preferred compounds are those having the following formulae (a)—(s) and their mirror images.

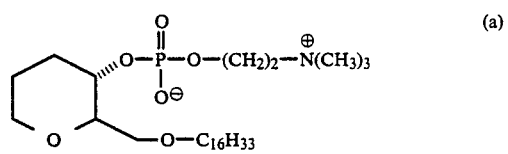
(a)

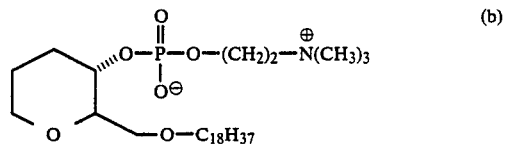
(b)

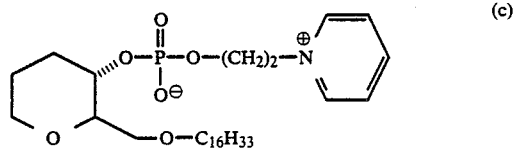
(c)

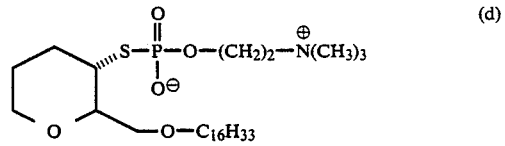
(d)

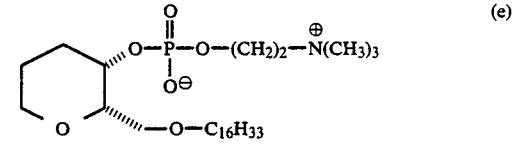
(e)

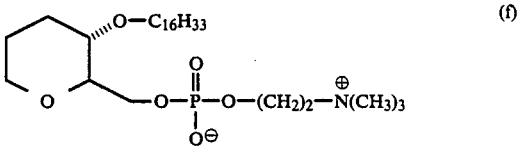
(f)

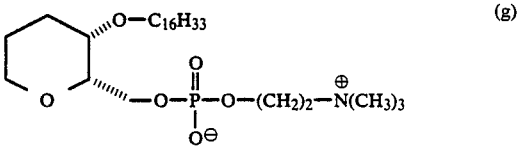
(g)

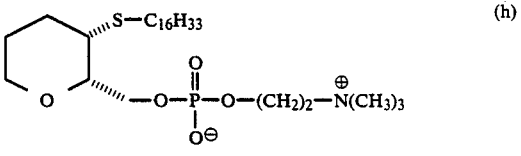
(h)

(i) 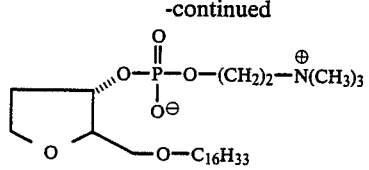
(j) 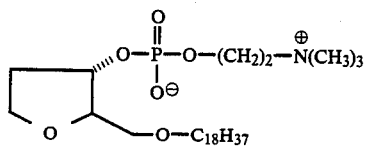
(k) 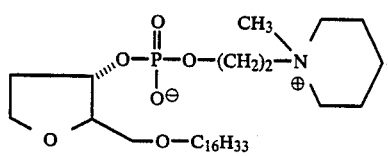
(l) 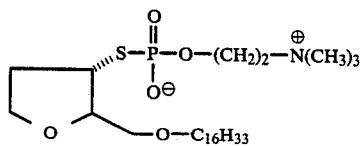
(m) 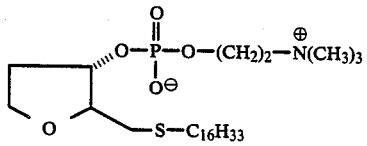
(n) 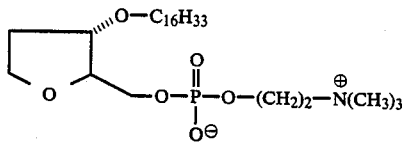
(o) 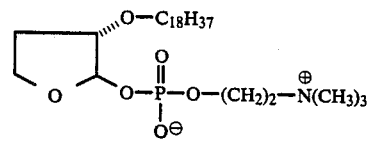
(p) 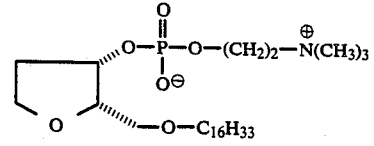
(q) 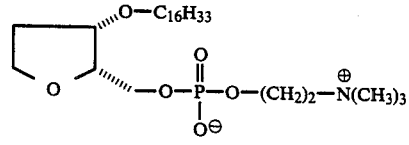
(r) 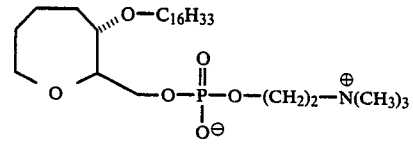
(s) 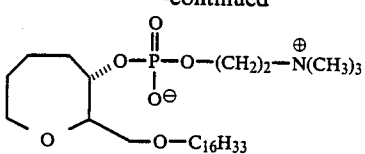
Of the compounds shown above, compounds (a), (c), (e), (f) and (i) and their mirror images (a'), (c'), (e'), (f') and (i') are particularly preferred:
(k) 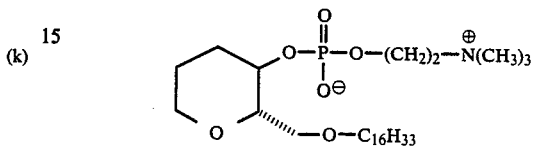
(l) 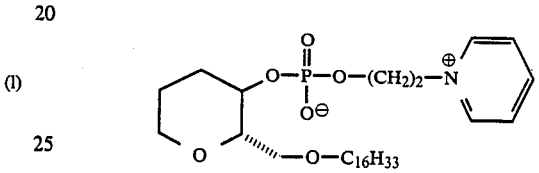
(m) 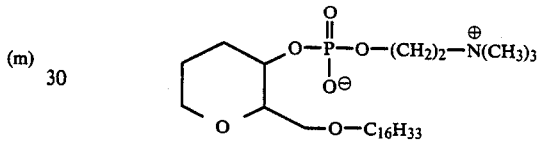
(n) 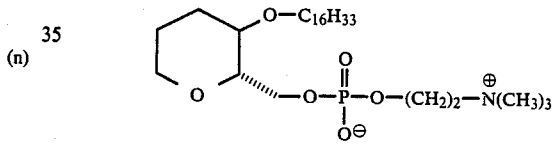
(o) 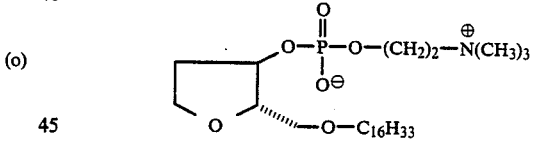
The compounds of the present invention may be prepared as illustrated by the following reaction scheme:
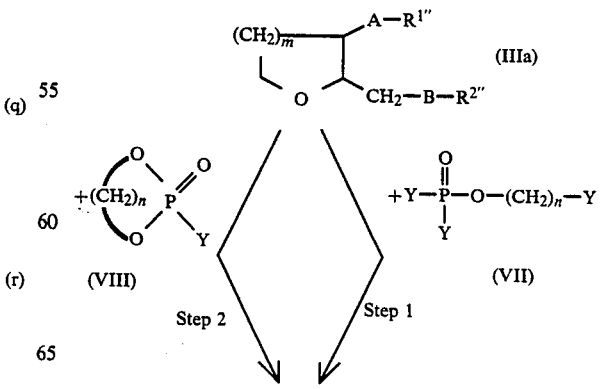

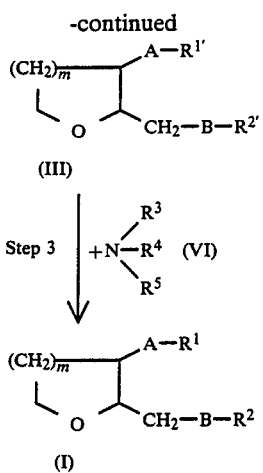

In the above formulae, $R^1$, $R^2$, $R^3$, $R^4$, $R^5$, $R^{1'}$, $R^{2'}$, A, B, Y, m and n are as defined above. One of $R^{1''}$ and $R^{2''}$ represents an alkyl group having from 10 to 22 carbon atoms (the same as $R^1$ or $R^2$) and the other represents a hydrogen atom. In the case of the compound of formula (VII), the three halogen atoms represented by Y may be the same or different. The nature of the halogen atom represented by Y is not particularly critical, since these halogen atoms are eliminated during the reaction; suitable halogen atoms include the chlorine, bromine and iodine atoms.

Steps 1 and 2 of this reaction scheme are alternatives. In step 1, the hydroxy or mercapto group, —AH or —BH, of the cyclic ether of formula (IIIa) is reacted with a haloalkyl phosphorodichloridate of formula (VII) and the product of this reaction is then treated with water, to give the compound of formula (III) in which $R^{1'}$ or $R^{2'}$ represents the aforementioned group of formula (IV). Alternatively, in step 2, the compound of formula (IIIa) is reacted with the cyclic phosphoryl halide, preferably chloride, of formula (VIII), to give the compound of formula (III) in which $R^{1'}$ or $R^{2'}$ represents the aforementioned group of formula (V).

Both reactions are preferably effected in the presence of a solvent, the nature of which is not critical, provided that it does not adversely affect the reaction and that it can dissolve the reagents, at least to some degree. Preferred solvents are: halogenated hydrocarbons, preferably halogenated aliphatic hydrocarbons, such as methylene chloride, chloroform or 1,2-dichloroethane; ethers, such as diethyl ether, tetrahydrofuran or dioxane; and aromatic hydrocarbons, such as benzene or toluene.

Both reactions are preferably also effected in the presence of a base, the nature of which is not particularly critical, provided that it does not adversely affect the reagents. Suitable bases include amines, particularly triethylamine, diethylamine or pyridine.

Both reactions will take place over a wide range of temperatures, and the specific temperature chosen is not particularly critical. In the case of the reaction involving the haloalkyl phosphorodichloridate of formula (VII), the preferred temperature is within the range from 0° to 120° C. In the case of the reaction involving the cyclic phosphoryl halide of formula (VIII), the preferred temperature is within the range of from 20° to 120° C.

The time required for the reaction will vary, depending upon many factors, including the nature of the reagents, solvent and base employed, as well as the reaction temperature. However, within the reaction temperatures indicated above, both reactions will normally be complete within a period of from 2 to 24 hours.

After completion of the reaction, the resulting compound of formula (III) can be isolated from the reaction mixture by conventional means. For example, the solution containing the desired product may be concentrated by evaporating off the solvent under reduced pressure and then the residue purified by such conventional techniques as the chromatography techniques, particularly silica gel column chromatography or recrystallization.

In step 3 of the reaction scheme, the ω-haloalkyl phosphate of formula (III) [$R^{1'}$ or $R^{2'}$ represents the aforementioned group of formula (IV)] or cyclic phosphate of formula (III) [$R^{1'}$ or $R^{2'}$ represents the aforementioned group of formula (V)] is reacted with the amine of formula (VI) in a suitable solvent to give the desired compound of formula (I), which may be in the form of an inner salt.

There is no particular limitation on the nature of the solvent to be employed, provided that it has no adverse effect upon the reaction and that it can dissolve the reagents, at least to some degree. Suitable solvents include: halogenated hydrocarbons, preferably halogenated aliphtic hydrocarbons, such as methylene chloride or chloroform; lower alkanols, such as methanol, ethanol or isopropanol; amides, such as dimethylformaide; ethers, such as diethyl ether, tetrahydrofuran or dioxane; nitriles, such as acetonitrile; and water. a single one of these solvents or a mixture of any two or more, e.g. two or three, thereof may be employed. For example, a suitable mixture might be chloroform, dimethylformamide and isopropanol in an appropriate ratio, e.g. a volume ratio of about 3:5:5.

The temperature at which the reaction is carried out is not particularly critical, although we generally prefer to carry out the reaction at a temperature of from 20° to 80° C. The reaction is preferably effected in a nitrogen atmosphere and preferably in a tightly sealed container (e.g. a sealed tube). The time required for the reaction will vary over a wide range, depending upon the reagents and solvent employed and the reaction temperature, but a period of from 1 to 48 hours will normally suffice.

After completion of the reaction, the product of this reaction, which may be the compound of formula (I) itself (i.e. the inner salt) or may be a salt thereof, may be isolated from the reaction mixture by conventional means. For example, a suitable recovery technique would comprise concentrating the reaction mixture by evaporating off the solvent under reduced pressure and then purifying the residue by conventional techniques, such as the various chromatography techniques and especially silica gel column chromatography.

In the case of the reaction involving the cyclic phosphate of formula (III) [$R^{1'}$ or $R^{2'}$ represents the aforementioned group of formula (V)], the inner salt of formula (I) will normally be obtained directly. Similarly, in the case of the reaction involving the ω-haloalkyl phosphate of formula (III) [$R^{1'}$ or $R^{2'}$ represents the aforementioned group of formula (IV)] and where the amine of formula (VI) is pyridine, the inner salt will normally be obtained directly.

However, in other cases involving the ω-haloalkyl phosphate of formula (III) [$R^{1'}$ or $R^{2'}$ represents the aforementioned group of formula (IV)], the product of step 3 will normally be a salt of the compound of formula (I), i.e. $R^1$ or $R^2$ will represent a group of formula (IIa). In this case, if the inner salt itself is desired, this may be produced by treating its salt with an ion-exchange resin (for example resin MB-3, produced by Rohm and Haas Co.) or with a silver salt (for example silver carbonate or silver acetate).

If desired, the compound of formula (I) or salt thereof may be converted to a salt of any other ion by known methods.

The cyclic ether compounds of formula (IIIa) used as starting materials in the above sequence of reactions are novel compounds and can be prepared from compounds of formula (IX), shown in the following reaction schemes (specifically, 3,4-dihydro-2H-pyran, dihydrofuran or 6,7-dihydrooxepine) can be prepared stereospecifically (with respect to the two asymmetric carbon atoms identified above) by any of the reaction schemes shown below:

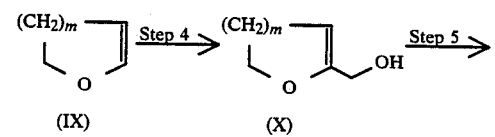

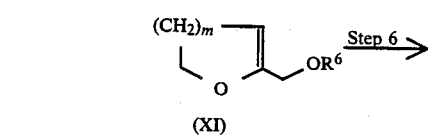

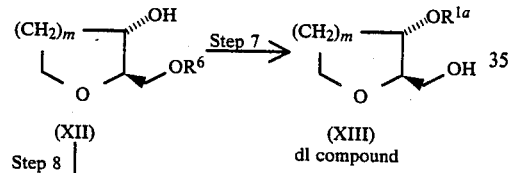

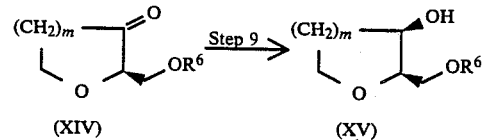

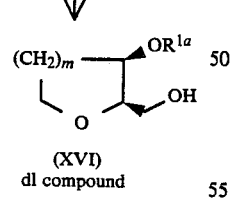

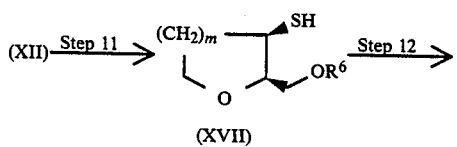

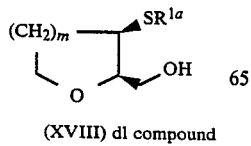

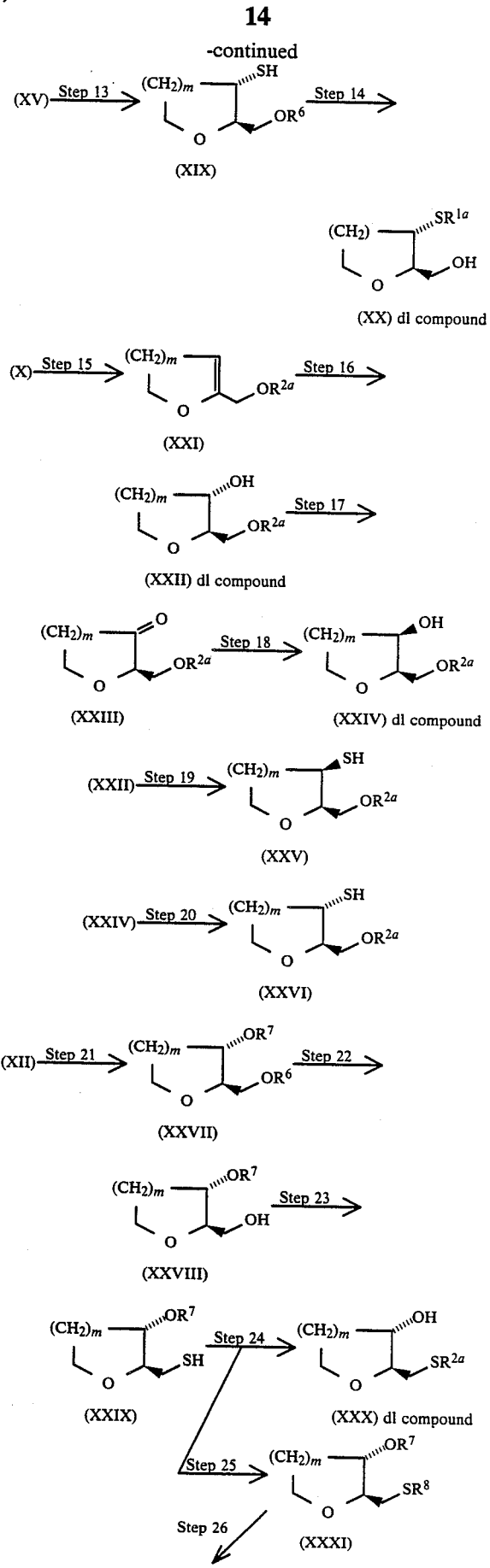

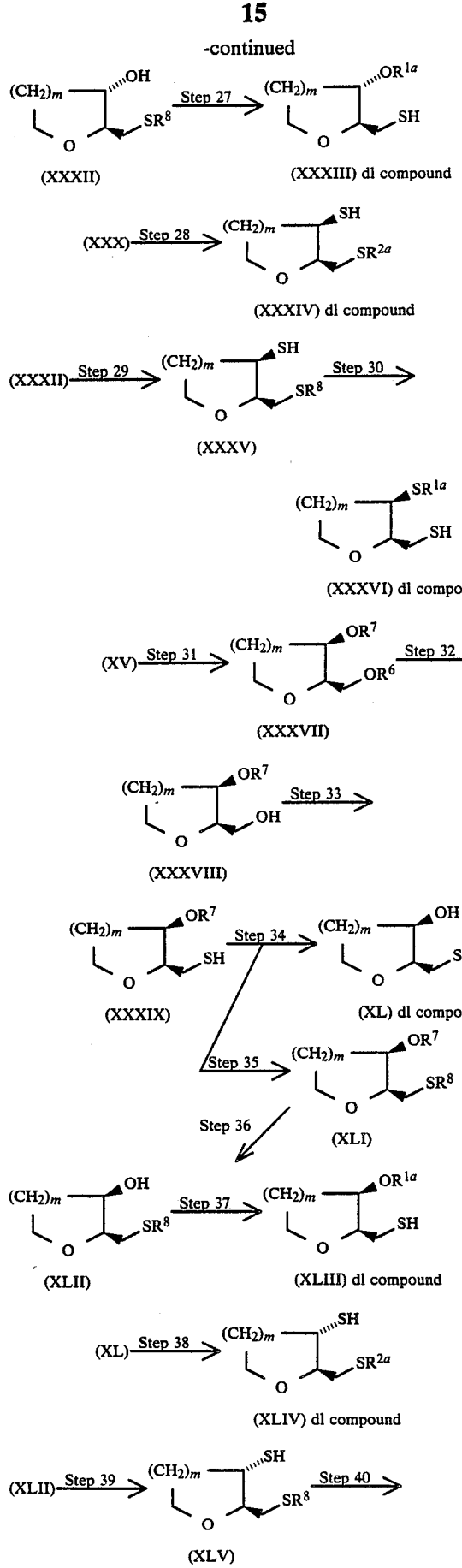

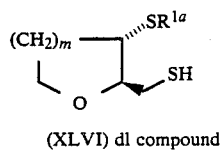

(XLVI) dl compound

In these formulae, m is as defined above. $R^{1a}$ and $R^{2a}$ each represent $C_{10}$–$C_{22}$ alkyl groups, which may be straight or branched chain alkyl groups (the same as $R^1$ and $R^2$).

$R^6$ and $R^7$ are both hydroxy-protecting groups, whilst $R^8$ represents a mercapto-protecting group. Where $R^6$ and $R^7$ or $R^7$ and $R^8$ occur within the same compound, the protecting groups are preferably selected from different classes, so that one protecting group may be removed preferentially, without removing the other.

Examples of classes of hydroxy-protecting groups which may be employed include: di- and tri-arylmethyl groups, for example the diphenylmethyl (=benzhydryl), triphenylmethyl, α-naphthyldiphenylmethyl, p-methoxyphenyldiphenylmethyl, and p-(p-bromophenacyloxy)phenyldiphenylmethyl groups; optionally substutited tetrahydropyranyl groups, such as the tetrahydropyran-2-yl, 3-bromotetrahydropyran-2-yl, 4-methoxytetrahydropyran-4-yl, tetrahydrothiopyran-2-yl and 4-methoxytetrahydrothiopyran-2-yl groups; trialkylsilyl groups, in which each alkyl part is preferably $C_1$–$C_4$, for example the trimethylsilyl, triethylsilyl, isopropyldimethylsilyl, t-butyldimethylsilyl, methyldiisopropylsilyl, methyldi-t-butylsilyl and triisopropylsilyl groups; and optionally substituted benzyl groups, for example the benzyl, p-methoxybenzyl, o-nitrobenzyl, p-nitrobenzyl, p-halobenzyl and p-cyanobenzyl groups.

Preferred examples of mercapto-protecting groups which may be represented by $R^8$ include the aforementioned benzyl groups and di- and tri-arylmethyl groups; also included amongst the preferred mercapto-protecting groups are lower (e.g. $C_2$–$C_5$) aliphatic acyl groups, such as the acetyl group.

We particularly prefer that $R^6$ should be one of the aforementioned optionally substituted benzyl groups, $R^7$ should be one of the aforementioned optionally substituted tetrahydropyranyl groups and $R^8$ should be one of the lower aliphatic acyl groups. More preferably, $R^6$ is a benzyl group, $R^7$ is a tetrahydropyran-2-yl group and $R^8$ is an acetyl group.

Since many of the reactions involved in the above reaction schemes are repeated, they may be summarized as follows:

Reaction 1

In this reaction, the compound of formula (IX) is subjected to hydroxymethylation, to prepare the compound of formula (X) by the method of A. Lebouc et al. [A. Lebouc et al., Synthesis, 610 (1979)].

Reaction 2

In this reaction, the hydroxy group of the compound of formula (X) or the mercapto group of the compound of formula (XXIX) may be protected with any one of the appropriate protecting groups mentioned above to prepare the compound of formula (XI) or the compound of formula (XXXI), respectively. These reactions may be carried out by conventional means for introduction of protecting groups, for example, in the case of protecting the hydroxy group, preferably benzylation using a benzyl halide.

Reaction 3

In this reaction, the starting material, for example the compound of formula (XI), is subjected to a hydroboration reaction to introduce a trans-hydroxy group onto the double bond and give, for example, the compound of formula (XII). This reaction is involved in several of the steps in the above reaction scheme.

Reaction 4

In this reaction, a hydroxy group, for example of the compound of formula (XII), is alkylated with an alkyl halide (e.g. hexadecyl bromide). The same reaction may also be effected to alkylate a mercapto group, for example of the compound of formula (XVII).

Reaction 5

In this reaction, a hydroxy-protecting or mercapto-protecting group is removed, for example the hydroxy-protecting group is removed from the compound of formula (XII). The nature of the removal reaction depends upon the particular class of hydroxy-protecting group or mercapto-protecting group involved and the nature of such reactions is well-known to those skilled in the art. For example, if the hydroxy-protecting group is one of the aforementioned di- or tri-arylmethyl groups, it may be removed by treatment with an acid such as trifluoroacetic acid, acetic acid or hydrochloric acid. If the hydroxy-protecting group is one of the aforementioned optionally substituted benzyl groups, it may be removed by reduction, preferably catalytic reduction, using palladium-on-carbon as the catalyst. If the hydroxy-protecting group is a trialkylsilyl group, it may be removed by treatment with a compound generating fluoride anions, preferably tetrabutylammonium fluoride. If the hydroxy-protecting group is one of the aforementioned optionally substituted tetrahydropyranyl groups, it may be removed by treatment with an acid, for example acetic acid or p-toluenesulfonic acid. As is well known, optionally substituted benzyl groups which protect a hydroxy group are usually removed by reduction. However, in the presence of a mercapto or protected mercapto group in the same molecule, the reducing agents used for deprotecting these protected hydroxy groups become rather inactive, adversely affected by the mercapto or protected mercapto group. Consequently, where the compound contains both a mercapto-protecting group and a hydroxy-protecting group and it is desired to remove the hydroxy-protecting group, then the reaction with aluminum chloride and sodium iodide is employed if the hydroxy-protecting group is one of the optionally substituted benzyl groups, whilst the reaction with an acid is employed if the hydroxy-protecting group is one of the di- or tri-arylmethyl groups. The mercapto-protecting group, preferably acetyl group, may be removed by treatment with a base, such as methanolic sodium methoxide, aqueous ammonia, aqueous sodium hydroxide or aqueous potassium hydroxide, preferably a 10–30% w/w methanolic solution of sodium methoxide.

Reaction 6

In this reaction, the hydroxy group of the compound of formula (XII) is oxidized to a carbonyl group by means of Jones' reagent, using chromic acid or pyridinium chlorochromate, to prepare the compound of formula (XIV).

Reaction 7

In this reaction, the carbonyl group of the compound of formula (XIV) is reduced stereoselectively, using L-selectride, to form a cis-hydroxy group and give the compound of formula (XV).

Reaction 8

In this reaction, a hydroxy group, for example a hydroxy group of the compound of formula (XII), can be acylated, for example methanesulfonylated, toluenesulfonylated, trifluoromethanesulfonylated or trifluoroacetylated, to form an ester, and then the resulting acyloxy group can be converted to a protected mercapto group whose configuration is inverted, compared to the original hydroxy group, using, for example thioacetic acid. This reaction may be employed in a number of steps in the above reaction schemes.

Reaction 9

In this reaction a free hydroxy group, of a compound already containing one protected hydroxy group, for example the free hydroxy group of the compound of formula (XII), may be protected by a different hydroxy-protecting group in order to prepare the compound of formula (XXVII). In this case, the preferred protecting group is one selected from the class of optionally substituted tetrahydropyranyl groups.

The following Table 7 shows the reactions which may be employed for each of the steps of the reaction schemes given above.

TABLE 7

| Step | Reaction used | Step | Reaction used | Step | Reaction used |
|------|---------------|------|---------------|------|---------------|
| 4  | 1    | 17 | 6    | 30 | 4, 5 |
| 5  | 2    | 18 | 7    | 31 | 9    |
| 6  | 3    | 19 | 8, 5 | 32 | 5    |
| 7  | 4, 5 | 20 | 8, 5 | 33 | 8, 5 |
| 8  | 6    | 21 | 9    | 34 | 4, 5 |
| 9  | 7    | 22 | 5    | 35 | 2    |
| 10 | 4, 5 | 23 | 8, 5 | 36 | 5    |
| 11 | 8, 5 | 24 | 4, 5 | 37 | 4, 5 |
| 12 | 4, 5 | 25 | 2    | 38 | 8, 5 |
| 13 | 8, 5 | 26 | 5    | 39 | 8, 5 |
| 14 | 4, 5 | 27 | 4, 5 | 40 | 4, 5 |
| 15 | 4    | 28 | 8, 5 |    |      |
| 16 | 3    | 29 | 8, 5 |    |      |

The compounds of the present invention are effective in the chemotherapy tumors. For administration, the compounds of the invention may be formulated, e.g. as tablets, capsules, granules, powders or syrups, for oral administration, or as injectible solutions or suspensions or suppositories for parenteral administration. Although the preferred dose will vary, depending upon the symptoms, age, condition and bodyweight of the patient, as well as the route of administration, a preferred dose would normally be expected to be from 0.1 to 100 mg/kg bodyweight per day, and this could be administered in a single dose or in divided doses.

The invention is further illustrated by the following non-limiting Examples. Preparation of certain of the starting materials employed in these Examples is illustrated by the subsequent Preparations. The biological activities of certain of the compounds of the invention are then illustrated in the subsequent Experiments 1–3.

EXAMPLE 1 dl-(trans-2-Hexadecyloxymethyltetrahydropyran-3-yl) 2-(trimethylammonio)ethyl phosphate 3.63 g of 2-bromoethyl phosphorodichloridate were added dropwise, whilst ice-cooling, to a solution of 2.09 ml of triethylamine and 3.566 g of dl-trans-2-hexadecyloxymethyl-3-hydroxytetrahydropyran (prepared as described in Preparation 2) in 75 ml of methylene chloride. The reaction mixture was stirred at room temperature for 16 hours, and then 0.5 ml of triethylamine and 2 ml of water were added, and the resulting mixture was heated under reflux for 1 hour. The reaction mixture was then cooled and washed with 10% v/v aqueous hydrochloric acid. The aqueous layer was separated and extracted with methylene chloride. The organic layer and the extract were combined, washed with water and dried. The solvent was distilled off and the oily residue (about 5 g) was subjected to column chromatography using 150 g of silica gel. The fractions eluted with mixtures of methylene chloride and methanol ranging from 20:1 to 10:1 by volume were collected to give 2.425 g of dl-(trans-2-hexadecyloxymethyltetrahydropyran-3-yl) 2-bromoethyl phosphate as an oily substance.

Elemental Analysis: Calculated for $C_{24}H_{48}BrO_6P \cdot 3/2H_2O$: C, 50.52%; H, 9.01%; Br, 14.00%; P, 5.43%. Found: C, 50.85%; H, 8.84%; Br, 14.13%; P, 5.75%.

0.914 g of the compound prepared as described above was dissolved in 26 ml of a 5:5:3 by volume mixture of dimethylformamide, isopropanol and chloroform, and trimethylamine gas (about 4 g) was introduced into the solution, whilst ice-cooling. The resulting solution was heated under nitrogen, with stirring, at 50° C. for 5 hours.

After the reaction mixture had been cooled, 0.358 g of silver carbonate was added, and the mixture was heated under reflux for 1 hour. It was then cooled and the solvent was removed by evaporation under reduced pressure. 30 ml of methanol were added to the residue. The insoluble residue was filtered off and the methanol was removed by distillation under reduced pressure. The oily residue was subjected to column chromatography through 20 g of silica gel. The fraction eluted with a 60:35:5 by volume mixture of methylene chloride, methanol and water gave 0.386 g of the title compound as a white powder, melting at 220°–224° C.

Nuclear Magnetic Resonance Spectrum (CD₃OD) δ ppm: 0.7–1.9 (34H, multiplet); 2.20–2.55 (1H, multiplet); 3.23 [9H, singlet, —N⁺(CH₃)₃]; 3.3–4.1 (10H, multiplet); 4.27 (2H, multiplet).

Fast Atom Bombardment Mass Spectrum: QM⁺522 (M+H).

Elemental Analysis: Calculated for $C_{27}H_{56}NO_6P \cdot H_2O$: C, 60.08%; H, 10.83%; N, 2.60%; P, 5.74%. Found: C, 59.97%; H, 10.59%; N, 2.48%; P, 5.68%.

EXAMPLE 2 dl-(cis-2-Hexadecyloxymethyltetrahydropyran-3-yl) 2-(trimethylammonio)ethyl phosphate Following the procedure described in Example 1, the phosphorylation of 1.069 g of dl-cis-2-hexadecyloxymethyl-3-hydroxytetrahydropyran (prepared as described in Preparation 4) gave 0.237 g of dl-(cis-2-hexadecyloxymethyltetrahydropyran-3-yl) 2-bromoethyl phosphate. This substance was allowed to react with trimethylamine by the same procedure as described in Example 1, to give 0.063 g of the title compound as a white powder, melting at 225°–231° C.

Nuclear Magnetic Resonance Spectrum (CD₃OD) δ ppm: 0.7–1.7 (32H, multiplet); 1.73–2.43 (3H, multiplet); 3.25 [9H, singlet, —N⁺(CH₃)₃]; 3.40–3.80 (9H, multiplet); 3.82–4.15 (1H, multiplet); 4.15–4.45 (2H, multiplet).

Elemental Analysis: Calculated for $C_{27}H_{56}NO_6P \cdot H_2O$: C, 60.08%; H, 10.83%; N, 2.60%; P, 5.74%. Found: C, 59.97%; H, 10.59%; N, 2.48%; P, 5.68%.

EXAMPLE 3 dl-(trans-3-Hexadecyloxytetrahydropyran-2-yl)methyl 2-(trimethylammonio)ethyl phosphate Following the procedure described in Example 1, the phosphorylation of 1.253 g of dl-trans-3-hexadecyloxy-2-hydroxymethyltetrahydropyran (prepared as described in Preparation 8) gave 1.504 g of dl-(trans-3-hexadecyloxytetrahydropyran-2-yl)methyl 2-bromoethyl phosphate. This substance was allowed to react with trimethylamine by the same procedure as described in Example 1, to give 1.089 g of the title compound as a white powder, melting at 85°–92° C. (it became resin-like after melting).

Nuclear Magnetic Resonance Spectrum (CD₃OD) δ ppm: 0.17–1.85 (34H, multiplet); 2.03–2.55 (1H, multiplet); 3.23 [9H, singlet, —N⁺(CH₃)₃]; 3.33–4.16 (10H, multiplet); 4.16–4.50 (1H, multiplet).

Elemental Analysis: Calculated for $C_{27}H_{56}NO_6P \cdot 2H_2O$: C, 58.14%; H, 10.84%; N, 2.51%; P, 5.55%. Found: C, 58.61%; H, 10.46%; N, 2.68%; P, 5.53%.

EXAMPLE 4 dl-(cis-3-Hexadecyloxytetrahydropyran-2-yl)methyl 2-(trimethylammonio)ethyl phosphate Following the procedure described in Example 1, the phosphorylation of 1.409 g of dl-cis-3-hexadecyloxy-2-hydroxymethyltetrahydropyran (prepared as described in Preparation 11) gave 1.579 g of impure dl-(cis-3-hexadecyloxytetrahydropyran-2-yl)methyl 2-bromoethyl phosphate. This substance was allowed to react with trimethylamine by the same method as described in Example 1, to give 0.993 g of the title compound as a white powder, melting at 213°–220° C.

Nuclear Magnetic Resonance Spectrum (CD₃OD) δ ppm: 0.8–1.77 (33H, multiplet); 1.80–2.30 (2H, multiplet); 3.23 [9H, singlet, —N⁺(CH₃)₃]; 3.37–3.75 (5H, multiplet); 2.80–4.23 (3H, multiplet); 4.13–4.45 (2H, multiplet).

Elemental Analysis: Calculated for $C_{27}H_{56}NO_6P \cdot H_2O$: C, 60.08%; H, 10.83%; N, 2.60%; P, 5.74%. Found: C, 59.7%; H, 10.68%; N, 2.56%; P, 6.05%.

EXAMPLE 5 dl-(trans-2-Hexadecyloxymethyltetrahydrofuran-3-yl) 2-(trimethylammonio)ethyl phosphate A solution containing 1.275 g of dl-trans-2-hexadecyloxymethyl-3-hydroxytetrahydrofuran (prepared as described in Preparation 14), 1.060 g of 2-chloro-2-oxo-1,3,2-dioxaphospholane and 1.30 ml of diisopropylethylamine in 20 ml of 1,2-dichloroethane was heated, with stirring, at 80° C. for 16 hours. The mixture was then cooled, and the solvent was removed by distillation under reduced pressure. The residue was then dissolved in 15 ml of acetonitrile. 3.0 g of trimethylamine gas were passed through and dissolved in the solution, and the resulting reaction mixture was heated in a sealed tube at 80° C. for 18 hours. It was then cooled, and the reaction mixture was evaporated to dryness. The residue was subjected to column chromatography using 50 g of silica gel. The crude substance obtained from the fraction eluted with a 60:35:5 by volume mixture of methylene chloride, methanol and water was further purified by chromatography through two silica gel Lobar B columns. The fraction eluted with the same solvent system as described above gave 1.257 g of the title compound as a white powder, melting at 213°–223° C.

Nuclear Magnetic Resonance Spectrum (CD$_3$OD) δ ppm: 0.7–1.75 (31H, multiplet); 1.95–2.30 (2H, multiplet); 3.25 [9H, singlet, —N$^+$(CH$_3$)$_3$]; 3.38–3.80 (6H, multiplet); 3.80–4.15 (3H, multiplet); 4.15–4.45 (2H, multiplet); 4.55–4.80 (1H, multiplet).

Elemental Analysis: Calculated for C$_{26}$H$_{54}$NO$_6$P.·H$_2$O: C, 59.40%; H, 10.74%; N, 2.66%; P, 5.89%. Found: C, 59.60%; H, 10.75%; N, 2.67%; P, 5.80%.

EXAMPLE 6 dl-(trans-2-Hexadecyloxymethyltetrahydropyran-3-yl) 2-pyridinioethyl phosphate 1.512 g of dl-trans-2-hexadecyloxymethyltetrahydropyran-3-yl 2-bromoethyl phosphate (prepared as described in the first half of Example 1) was dissolved in 20 ml of pyridine, and the resulting solution was heated, with stirring, at 80° C. for 20 hours. The mixture was then cooled and the pyridine was removed by distillation under reduced pressure. The residue was subjected to column chromatography through 45 g of silica gel. The fraction eluted with a 60:35:5 by volume mixture of methylene chloride, methanol and water gave 1.422 g of the title compound as a white powder, melting at 123°–129° C.

Nuclear Magnetic Resonance Spectrum (CD$_3$OD) δ ppm: 0.7–1.8 (34H, multiplet); 2.05–2.35 (1H, multiplet); 3.45 (2H, triplet, J=6.5 Hz); 3.50–4.05 (4H, multiplet); 4.20–4.45 (2H, multiplet); 4.75–4.95 (2H, multiplet); 8.13 (2H, multiplet); 8.63 (1H, multiplet); 9.03 (H, multiplet).

Elemental Analysis: Calculated for C$_{29}$H$_{53}$NO$_6$P.3/2H$_2$O: C, 61.13%; H, 9.64%; N, 2.46%; P, 5.44%. Found: C, 61.33%; H, 9.59%; N, 2.45%; P, 5.17%. Br, 0%.

EXAMPLE 7 dl-(cis-3-Hexadecylthiotetrahydropyran-2-yl)methyl 2-(trimethylammonio)ethyl phosphate A solution containing 689 mg of 2-chloro-2-oxo-1,3,2-dioxaphospholane dissolved in 9 ml of 1,2-dichloroethane was added dropwise, whilst ice-cooling, to a solution of 900 mg of dl-cis-3-hexadecylthio-2-hydroxymethyltetrahydropyran (prepared as described in Preparation 18) in 18 ml of 1,2-dichloroethane. The reaction mixture was then stirred at 80° C. for 23 hours, after which it was cooled and the solvent was distilled off. The residue was dissolved in 15 ml of acetonitrile, and 5.97 g of trimethylamine gas was introduced into it, whilst ice-cooling. The reaction mixture was then heated at 80° C. for 40 hours in a sealed tube, after which it was cooled, and the solution was evaporated to dryness. The residue was subjected to column chromatography through 30 g of silica gel. The crude product obtained from the fraction eluted with a 160:35:5 by volume mixture of methylene chloride, methanol and water was further purified through a silica gel Lobar B column, and the fraction eluted with the same solvent as described above gave 1.080 g of the title compound as a white powder, melting at 208°–215° C. (with decomposition).

Nuclear Magnetic Resonance Spectrum (CD$_3$OD) δ ppm: 0.7–2.4 (35H, multiplet); 2.53 (2H, triplet, J=7 Hz); 2.92 (1H, multiplet); 3.23 [9H, singlet, —N$^+$(CH$_3$)$_3$]; 3.4–4.5 (9H, multiplet).

Mass spectrum (m/e): 538 (M$^+$+1).

PREPARATION 1

6-Hexadecyloxymethyl-3,4-dihydro-2H-pyran 5.71 g of 6-hydroxymethyl-3,4-dihydro-2H-pyran, 16.79 g of hexadecyl bromide and 8.22 g of pulverized 85% potassium hydroxide were mixed in 160 ml of toluene and heated under reflux for 2 hours. The mixture was then cooled, washed with water, dried and condensed by evaporation under reduced pressure. The resulting oily residue, 17 g, was subjected to column chromatography through 400 g of silica gel. The fraction eluted with a 1:5 by volume mixture of diethyl ether and hexane gave 14.38 g of the title compound as a colorless oily substance.

Nuclear Magnetic Resonance Spectrum (CDCl$_3$) δ ppm: 0.7–2.2 (35H, multiplet); 3.42 (2H, triplet, J=6 Hz); 3.80 (2H, singlet); 4.01 (2H, multiplet); 4.77 (1H, triplet, J=3.5 Hz).

Elemental Analysis: Calculated for C$_{22}$H$_{42}$O$_2$: C, 78.04%; H, 12.50%. Found: C, 77.84%; H, 12.39%.

PREPARATION 2 dl-trans-2-Hexadecyloxymethyl-3-hydroxytetrahydropyran 11 ml of a 1M tetrahydrofuran solution of borane was added dropwise, whilst ice-cooling, to a solution of 5.53 g of 6-hexadecyloxymethyl-3,4-dihydro-2H-pyran (prepared as described in Preparation 1) dissolved in 12 ml of tetrahydrofuran. The reaction mixture was stirred at room temperature for 3 hours, after which 4 ml of a 3N aqueous solution of sodium hydroxide were added to it, and then 4 ml of 30% hydrogen peroxide were added dropwise into it at 30°–40° C. The reaction mixture was then stirred at room temperature for 1 hour, after which it was poured in water. The mixture was then washed with a saturated aqueous solution of sodium chloride, and then the organic layer was separated, dried and condensed by evaporation under reduced pressure. The oily residue was subjected to column chromatography through 100 g of silica gel. The fraction eluted with mixtures of ethyl acetate and hexane ranging from 1:5 to 1:2 by volume gave 5.18 g of the title compound as crystals. Recrystallization from hexane gave needles, melting at 41.5°–43° C.

Infrared Spectrum (CHCl$_3$) $\nu_{max}$ cm$^{-1}$: 3500.

Mass spectrum (m/e): 357 (M$^+$+1).

Elemental Analysis: Calculated for C$_{22}$H$_{44}$O$_3$: C, 74.10%; H, 12.43%. Found: C, 73.83%; H, 12.51%.

PREPARATION 3 dl-2-Hexadecyloxymethyltetrahydropyran-3-one 5 ml of Jones reagent (1.34 g as chromic anhydride) were added, whilst ice-cooling, to a solution of 4.30 g of dl-trans-2-hexadecyloxymethyl-3-hydroxytetrahydropyran (prepared as described in Preparation 2) in 20 ml of acetone. The mixture was then stirred at room temperature for 2 hours, after which 2 ml of isopropanol were added. The reaction mixture was then stirred for a further 10 minutes, after which it was diluted with 50 ml of ethyl acetate and then washed, in turn, with water, a saturated aqueous solution of sodium bicarbonate and a saturated aqueous solution of sodium chloride. It was then dried, and the solvent was removed by distillation.

The resulting oily residue, 4.5 g, was subjected to column chromatography through 100 g of silica gel. The fraction eluted with mixtures of ethyl acetate and hexane ranging from 1:10 to 3:20 by volume gave 3.73 g of the title compound, melting at 42°–43.5° C. (hexane).

Infrared Spectrum (CHCl$_3$) $\nu_{max}$cm$^{-1}$: 1725.

Mass spectrum (m/e): 354 (M$^+$).

Elemental Analysis: Calculated for C$_{22}$H$_{42}$O$_3$: C, 74.52%; H, 11.94%. Found: C, 74.41%; H, 12.01%.

PREPARATION 4 dl-cis-2-Hexadecyloxymethyl-3-hydroxytetrahydropyran 3.011 g of dl-2-hexadecyloxymethyltetrahydropyran-3-one (prepared as described in Preparation 3) were dissolved in 10 ml of tetrahydrofuran and cooled with ice. 12 ml of a 1M tetrahydrofuran solution containing L-selectride were added dropwise over 10 minutes, and the reaction mixture was then stirred at 0°–5° C. for 30 minutes and at room temperature for 60 minutes. The reaction mixture was then ice-cooled again, and 5 ml of a 10% w/v aqueous solution of sodium hydroxide were added at 5°–15° C. 5 ml of 30% hydrogen peroxide were added little by little at 15°–30° C. The mixture was stirred at room temperature for 2 hours, after which water was added, and the resulting mixture was separated. The water layer was extracted twice with diethyl ether. The organic layer and the extracts were combined, washed, dried and condensed by evaporation under reduced pressure. The residue, 2.84 g, was purified by chromatography using a silica gel Lobar C column. The fractions eluted with mixtures of ethyl acetate and hexane ranging from 1:4 to 1:3 by volume gave 2.381 g of the title compound as crystals, melting at 67.5°–68.5° C. (ethyl acetate).

Infrared Spectrum (CHCl$_3$) $\nu_{max}$cm$^{-1}$: 3480.

Mass spectrum (m/e): 357 (M$^+$+1).

Elemental Analysis: Calculated for C$_{22}$H$_{44}$O$_3$: C, 74.10%; H, 12.44%. Found: C, 73.86%; H, 12.63%.

PREPARATION 5

6-Benzyloxymethyl-3,4-dihydro-2H-pyran

A solution of 5.71 g of 6-hydroxymethyl-3,4-dihydro-2H-pyran in 100 ml of dimethylformamide was added dropwise, whilst ice-cooling, to a mixture of 2.18 g of a 55% w/w suspension of sodium hydride in mineral oil and 100 ml of dimethylformamide. The mixture was stirred at room temperature for 60 minutes, after which 6.33 g of benzyl chloride were added. The reaction mixture was stirred for 16 hours, and then poured into 1 liter of water and extracted twice with ethyl acetate. The extract was washed with water, dried and condensed by evaporation under reduced pressure. The oily residue, 13 g, was subjected to column chromatography through 200 g of silica gel. The fraction eluted with mixtures of diethyl ether and hexane ranging from 4:100 to 5:100 by volume gave 9.40 g of the title compound as a colorless oily substance, boiling at 125°–130° C. (bath temperature)/1 mmHg (133 Pa).

Nuclear Magnetic Resonance Spectrum (CDCl$_3$) $\delta$ ppm: 1.65–2.2 (4H, multiplet); 3.87 (2H, singlet); 4.03 (2H, multiplet); 4.57 (2H, singlet); 4.80 (1H, triplet, J=3.5 Hz); 7.2–7.6 (5H, multiplet).

Elemental Analysis: Calculated for C$_{13}$H$_{16}$O$_2$: C, 76.44%; H, 7.90%. Found: C, 76.36%; H, 7.90%.

PREPARATION 6 dl-trans-2-Benzyloxymethyl-3-hydroxytetrahydropyran

The hydroboration reaction described in Preparation 2 was repeated, but using 9.00 g of 6-benzyloxymethyl-3,4-dihydro-2H-pyran (prepared as described in Preparation 5). The resulting crude oily substance, 10.5 g, was subjected to column chromatography through 250 g of silica gel. The fraction eluted with a 1:20 by volume mixture of ethyl acetate and methylene chloride gave 8.82 g of the title compound, boiling at 130°–135° C. (bath temperature)/1 mmHg (133 Pa).

Nuclear Magnetic Resonance Spectrum (CDCl$_3$) $\delta$ ppm: 1.15–2.25 (4H, multiplet); 2.83 (1H, doublet, J=3 Hz); 3.1–3.6 (3H, multiplet); 3.68 (2H, doublet, J=5 Hz); 3.75–4.05 (1H, multiplet); 4.58 (2H, singlet); 7.2–7.5 (5H, multiplet).

Mass spectrum (m/e): 222 (M$^+$).

Elemental Analysis: Calculated for C$_{13}$H$_{18}$O$_2$: C, 70.24%; H, 8.16%. Found: C, 70.07%; H, 8.04%.

PREPARATION 7 dl-trans-2-Benzyloxymethyl-3-hexadecyloxytetrahydropyran

A solution of 2.22 g of dl-trans-2-benzyloxymethyl-3-hydroxytetrahydropyran (prepared as described in Preparation 6) in 10 ml of dimethylformamide was added dropwise, with ice-cooling, to 10 ml of dimethylformamide containing suspended in it 0.480 g of a 55% w/w suspension of sodium hydride in mineral oil. The reaction mixture was stirred at room temperature for 60 minutes, after which 5.49 g of hexadecyl bromide were added, and the resulting mixture was stirred for a further 4 hours. Finally, the mixture was stirred at 60° C. for 60 minutes and then cooled. It was then poured into 100 ml of water, and extracted twice with ethyl acetate. The extract was washed with water, dried and condensed by evaporation under reduced pressure. The oily residue was subjected to column chromatography resulting through 100 g of silica gel. The fraction eluted with mixtures of diethyl ether and hexane ranging from 1:20 to 1:10 by volume gave 3.82 g of the title compound as a solid having a low melting point, melting at 28.5°–29.5° C. (cold methanol).

Nuclear Magnetic Resonance Spectrum (CDCl$_3$) $\delta$ ppm: 0.7–2.4 (35H, multiplet); 3.0–4.2 (8H, multiplet); 4.60 (2H, AB-quartet, J=13 Hz); 7.2–7.45 (5H, multiplet).

Mass spectrum (m/e): 446 (M$^+$).

Elemental Analysis: Calculated for C$_{29}$H$_{50}$O$_3$: C, 77.97%; H, 11.28%. Found: C, 78.06%; H, 11.31%.

PREPARATION 8 dl-trans-3-Hexadecyloxy-2-hydroxymethyltetrahydropyran 1.5 g of 10% w/w palladium-on-activated carbon was added to a solution of 3.757 g of dl-trans-2-benzyloxymethyl-3-hexadecyloxytetrahydropyran (prepared as described in Preparation 7) in 150 ml of methanol, and the whole was mixed with hydrogen by shaking in a Paar's apparatus at room temperature under a pressure of 4 atmospheres (about 4 bars). After 20 hours, the catalyst was removed by filtration, and the solvent was then removed by distillation to give 2.749 g of the title compound as a solid, melting at 41°-42° C. (cold hexane).

Infrared Spectrum (CHCl$_3$) $\nu_{max}$cm$^{-1}$: 3600, 3470.
Mass spectrum (m/e): 357 (M$^+$+1), 356 (M$^+$).
Elemental Analysis: Calculated for C$_{22}$H$_{44}$O$_3$: C, 74.10%; H, 12.43%. Found: C, 74.12%; H, 12.11%.

PREPARATION 9 dl-cis-2-Benzyloxymethyl-3-hydroxytetrahydropyran

Jones oxidation was carried out by the same procedure as described in Preparation 3, but using 2.22 g of dl-trans-2-benzyloxymethyl-3-hydroxytetrahydropyran (prepared as described in Preparation 6). The crude substance, 2.08 g, obtained in this way was dissolved in 10 ml of tetrahydrofuran, and 12 ml of a 1M tetrahydrofuran solution containing L-selectride were added dropwise to this solution at 0°-5° C. Using the same procedure and purification as described in Preparation 4, 1.135 g of the title compound was obtained as a colorless liquid, boiling at 130°-140° C. (bath temperature)/1 mmHg (133 Pa).

Nuclear Magnetic Resonance Spectrum (CDCl$_3$) δ ppm: 1.25-2.30 (4H, multiplet); 2.68 (1H, doublet, J=6 Hz); 3.3-3.7 (4H, multiplet); 3.80 (1H, multiplet); 4.03 (1H, multiplet); 4.59 (2H, singlet); 7.2-7.5 (5H, multiplet).
Mass spectrum (m/e): 222 (M$^+$).

PREPARATION 10 dl-cis-2-Benzyloxymethyl-3-hexadecyloxytetrahydropyran

A mixture of 1.037 g of dl-cis-2-benzyloxymethyl-3-hydroxytetrahydropyran (prepared as described in Preparation 9), 1.709 g of hexadecyl bromide, 0.77 g of potassium hydroxide and 15 ml of toluene was heated, with stirring, at 120° C. for 10 hours. The reaction mixture was cooled and then poured into water. The water layer was extracted twice with diethyl ether. The organic layer and the extracts were combined, washed with water, dried and condensed by evaporation under reduced pressure. The resulting oily residue, 3.3 g, was subjected to column chromatography through 50 g of silica gel. The fraction eluted with a 1:10 by volume mixture of diethyl ether and hexane gave 1.455 g of the title compound as a colorless oily substance.

Nuclear Magnetic Resonance Spectrum (CDCl$_3$) δ ppm: 0.7-2.3 (35H, multiplet); 3.1-3.8 (5H, multiplet); 3.61 (2H, singlet); 3.85-4.15 (1H, multiplet); 4.55 (2H, AB-quartet, J=13 Hz); 7.2-7.5 (5H, multiplet).
Mass spectrum (m/e): 447 (M$^+$+1).
Elemental Analysis: Calculated for C$_{29}$H$_{50}$O$_3$: C, 77.97%; H, 11.28%. Found: C, 77.68%; H, 11.16%.

PREPARATION 11 dl-cis-3-Hexadecyloxy-2-hydroxymethyltetrahydropyran 1.409 g of dl-cis-2-benzyloxymethyl-3-hexadecyloxytetrahydropyran (prepared as described in Preparation 10) was dissolved in 100 ml of a 1:1 by volume mixture of methanol and ethanol. 0.70 g of a 10% w/w palladium-on-activated carbon catalyst was then added to the resulting solution. Catalytic reduction using the same procedure as described in Preparation 8 yielded 1.116 g of a crude substance, which was then subjected to column chromatography through 30 g of silica gel. The fraction eluted with mixtures of diethyl ether and hexane ranging from 1:20 to 1:5 by volume gave 1.031 g of the title compound, melting at 42°-43° C. (cold hexane).

Infrared Spectrum (CHCl$_3$) $\nu_{max}$cm$^{-1}$: 3600, 3460.
Mass spectrum (m/e): 357 (M$^+$+1), 356 (M$^+$).
Elemental Analysis: Calculated for C$_{22}$H$_{44}$O$_3$: C, 74.10%; H, 12.43%. Found: C, 73.85%; H, 12.13%.

PREPARATION 12

4,5-Dihydrofurfuryl alcohol 358 g of a 15.08% w/w solution of butyllithium in hexane were added dropwise over a period of 30 minutes to a solution of 58.7 g of dihydrofuran in 350 ml of anhydrous tetrahydrofuran, whilst maintaining the mixture at a temperature of from 5° to 10° C. by means of an ice-water bath. The reaction mixture was then heated, whilst stirring, at 50° C. for 2 hours, and then cooled again to 0° C. over an ice-water bath. 25.0 g of paraformaldehyde were then added at once to the mixture, and the resulting mixture was heated, whilst stirring, at 50° C. for 2 hours. The reaction mixture was then cooled and washed with 500 ml of ice-water. The aqueous layer was extracted 5 times with methylene chloride. The organic layer and the methylene chloride extracts were combined, dried and condensed by evaporation under reduced pressure. The oily residue, 14 g, was distilled under reduced pressure to give 8.97 g of the title compound as a colorless liquid, boiling at 66°-67° C./7 mmHg (930 Pa). As this compound tends to dimerize, it should be used immediately for the next step.

Nuclear Magnetic Resonance Spectrum (C$_6$D$_6$) δ ppm: 2.21 (2H, broad triplet, J=9 Hz); 2.98 (1H, broad triplet, J=6 Hz); 3.98 (2H, doublet, J=6 Hz); 4.00 (2H, triplet, J=9 Hz); 4.68 (1H, multiplet).
Mass spectrum: 200 (M×2), 101 (M$^+$+1), 100 (M$^+$).

PREPARATION 13

4,5-Dihydro-2-hexadecyloxymethylfuran

A solution of 4.09 g of 4,5-dihydrofurfuryl alcohol (prepared as described in Preparation 12) in 10 ml of dimethylformamide was added dropwise to 2.62 g of a 55% w/w suspension of sodium hydride in mineral oil, itself suspended in 40 ml of dimethylformamide, whilst maintaining the temperature of the mixture at from 5° to 12° C. by ice-cooling. The mixture was then stirred at room temperature for 30 minutes, 18.32 g of hexadecyl bromide were added to the solution, and the whole was stirred at room temperature for 15 hours. The reaction mixture was then poured into 200 ml of water, and extracted twice with diethyl ether. The extract was washed with water, dried and condensed by evaporation under reduced pressure. The oily residue, 17 g, was subjected to column chromatography through 400 g of Grade II-III alumina (a product of Woelm Pharma, West Germany). The fraction eluted with a 1:20 by volume mixture of diethyl ether and hexane gave 9.512 g of the title compound as a solid, melting at 30.5°-31.5° C. (cold hexane).

Nuclear Magnetic Resonance Spectrum (C$_6$D$_6$) δ ppm: 0.7-1.75 (31H, multiplet); 2.32 (2H, tripleting doubleting triplet, J$_1$=10, J$_2$=2, J$_3$=1.5 Hz); 3.40 (2H, triplet, J=6 Hz); 3.96 (2H, doublet of triplets, J$_1$=J$_2$=1.5 Hz); 4.11 (2H, triplet, J=10 Hz); 4.80 (1H, multiplet).
Mass spectrum (m/e): 324 (M$^+$).
Elemental Analysis: Calculated for C$_{21}$H$_{40}$O$_2$: C, 77.71%; H, 12.42%. Found: C, 77.70%; H, 12.28%.

PREPARATION 14 dl-trans-2-Hexadecyloxymethyl-3-hydroxytetrahydrofuran 9.296 g of 4,5-dihydro-2-hexadecyloxymethylfuran (prepared as described in Preparation 13) were subjected to a hydroboration reaction by the same procedure as described in Preparation 2. The crude substance, 10 g, was subjected to column chromatography through 300 g of silica gel. The fraction eluted with mixtures of ethyl acetate and hexane ranging from 1:10 to 1:3 by volume gave 7.025 g of the title compound as a solid, melting at 37.5°–38.5° C. (cold hexane).

Nuclear magnetic Resonance Spectrum (CDCl$_3$) δ ppm: 0.75–1.70 (31H, multiplet); 1.70–2.35 (2H, multiplet); 2.22 (1H, doublet, J=3 Hz); 3.32 (1H, doublet of doublets, J$_1$=9, J$_2$=6.5 Hz); 3.56 (1H, doublet of doublets, J$_1$=9, J$_2$=5 Hz); 3.47 (2H, triplet, J=7 Hz); 3.70–4.10 (3H, multiplet); 4.10–4.40 (1H, multiplet).

Mass spectrum (m/e): 343 (M$^+$+1).

Elemental Analysis: Calculated for C$_{21}$H$_{42}$O$_3$: C, 73.63%; H, 12.35%. Found: C, 73.52%; H, 12.62%.

PREPARATION 15 dl-cis-2-Benzyloxymethyl-3-acetylthiotetrahydropyran 1.04 ml of methanesulfonyl chloride was added dropwise, whilst ice-cooling, to a solution of 2.00 g of dl-trans-2-benzyloxymethyl-3-hydroxytetrahydropyran (prepared as described in Preparation 6) and 2.51 ml of triethylamine in 40 ml of benzene. The reaction mixture was stirred at room temperature for 1 hour, after which it was washed with water, dried and concentrated by evaporation under reduced pressure to give an oily crude mesylate.

Meanwhile 0.47 g of a 55% w/w suspension of sodium hydride in mineral oil was suspended in 5 ml of dimethylformamide. A solution of 0.77 ml of thioacetic acid in 5 ml of dimethylformamide was added dropwise to the suspension, whilst ice-cooling. The reaction mixture was stirred at room temperature for 1 hour, and then a solution of the whole of the above-mentioned crude mesylate in 10 ml of dimethylformamide was added and the mixture was heated, whilst stirring, at 80° C. for 16 hours, and then at 100° C. for 10 hours. The reaction mixture was then cooled, poured into water and extracted with ethyl acetate. The extract was washed with water, dried and evaporated to dryness under reduced pressure. The resulting oily residue was subjected to column chromatography through 50 g of silica gel. The fraction eluted with mixtures of diethyl ether and hexane ranging from 3:97 to 10:90 by volume was collected to give 1.448 g of the title compound as an oil substance.

Nuclear Magnetic Resonance Spectrum (CDCl$_3$) δ ppm: 1.10–2.20 (4H, multiplet); 2.30 (3H, singlet); 3.20–4.20 (6H, multiplet); 4.52 (2H, AB-quartet, J=12 Hz); 7.20–7.50 (5H, multiplet).

Infrared Spectrum (CHCl$_3$) ν$_{max}$cm$^{-1}$: 1685.

Mass spectrum (m/e): 280 (M$^+$).

Elemental Analysis: Calculated for C$_{15}$H$_{20}$O$_3$S: C, 64.26%; H, 7.19%; S, 11.44%. Found: C, 64.19%; H, 6.96%; S, 11.67%.

PREPARATION 16 dl-cis-2-Benzyloxymethyl-3-mercaptotetrahydropyran 1.04 ml of a methanolic solution containing about 28% w/w of sodium methoxide was added dropwise at −10° C. to a solution of 1.422 g of dl-cis-2-benzyloxymethyl-3-acetylthiotetrahydropyran (prepared as described in Preparation 15) in 30 ml of methanol. The reaction mixture was stirred at between −10° and 0° C. for 2 hours, after which 0.33 ml of methanesulfonic acid was added. The reaction mixture was then poured into water and extracted with ethyl acetate. The extract was washed with water, dried and concentrated by evaporation under reduced pressure. The oily residue thus obtained was subjected to column chromatography through 30 g of silica gel. The fraction eluted with mixtures of diethyl ether and hexane ranging from 3:97 to 5:95 by volume was collected to give 1.146 g of the title compound as an oil.

Nuclear Magnetic Resonance Spectrum (CDCl$_3$) δ ppm: 1.10–2.40 (4H, multiplet); 1.66 (1H, doublet, J=10 Hz); 2.95–3.25 (1H, multiplet); 3.25–3.85 (4H, multiplet); 3.85–4.20 (1H, multiplet); 4.55 (2H, AB-quartet, J=12 Hz); 7.10–7.50 (5H, multiplet).

Infrared Spectrum (CHCl$_3$) ν$_{max}$cm$^{-1}$: 2580.

Mass spectrum (m/e): 238 (M$^+$).

Elemental Analysis: Calculated for C$_{13}$H$_{18}$O$_2$S: C, 65.15%; H, 7.61%; S, 13.45%. Found: C, 65.62%; H, 7.83%; S, 13.19%.

PREPARATION 17 dl-cis-2-Benzyloxymethyl-3-hexadecylthiotetrahydropyran 0.27 g of a 55% w/w suspension of sodium hydride in mineral oil was suspended in 2 ml of dimethylformamide. To the suspension was added dropwise a solution of 1.210 g of dl-cis-2-benzyloxymethyl-3-mercaptotetrahydropyran (prepared as described in Preparation 16) in 5 ml of dimethylformamide, whilst ice-cooling the mixture. The reaction mixture was stirred at 60° C. for 1 hour, after which it was cooled to room temperature. A solution of 1.86 g of hexadecyl bromide in 3 ml of dimethylformamide was then added, and the mixture was stirred at room temperature for 1 hour. It was then poured into water and extracted with ethyl acetate. The extract was washed with water, dried and concentrated by evaporation under reduced pressure. The resulting residue was subjected to column chromatography through 40 g of silica gel. The fraction eluted with mixtures of diethyl ether and hexane ranging from 3:97 to 10:90 by volume was collected to give 2.284 g of the title compound as a solid.

Nuclear Magnetic Resonance Spectrum (CDCl$_3$) δ ppm: 0.8–2.1 (35H, multiplet); 2.46 (2H, broad triplet, J=7 Hz); 2.86 (1H, multiplet); 3.2–4.2 (5H, multiplet); 4.52 (2H, AB-quartet, J=12 Hz); 7.2–7.5 (5H, multiplet).

PREPARATION 18 dl-cis-3-Hexadecylthio-2-hydroxymethyltetrahydropyran 6.49 g of aluminum chloride, 7.29 g of sodium iodide and a solution of 2.250 g of dl-cis-2-benzyloxymethyl-3-hexadecylthiotetrahydropyran (prepared as described in Preparation 17) in 50 ml of methylene chloride were added, in that order, to a mixture of 100 ml of acetonitrile and 50 ml of methylene chloride. The reaction mixture was then stirred at room temperature for 2 hours, after which it was diluted with water, and filtered using a Celite (trade mark) filter aid. The filtrate was extracted with methylene chloride. The extract was washed with an aqueous solution of sodium thiosulfate and saturated aqueous solution of sodium chloride and dried. The extract was then concentrated by evaporation under reduced pressure, and the residue was subjected to column chromatography through 50 g of silica gel. The fraction eluted with mixtures of ethyl acetate and hexane ranging from 1:9 to 1:3 by volume was collected to give 1.736 g of the title compound as white crystals, melting at 52°–53° C. (hexane).

Nuclear Magnetic Resonance Spectrum (CDCl$_3$) δ ppm: 0.7–2.3 (36H, multiplet); 2.50 (2H, triplet, J=7 Hz); 2.86 (1H, multiplet); 3.3–4.2 (5H, multiplet).

Infrared Spectrum (CHCl$_3$) $\nu_{max}$cm$^{-1}$: 3590, 3450.

Mass spectrum (m/e): 372 (M+).

Elemental Analysis: Calculated for C$_{22}$H$_{44}$O$_2$S: C, 70.91%; H, 11.90%; S, 8.60%. Found: C, 70.63%; H, 11.92%; S, 8.82%.

EXPERIMENT 1

Anti-tumor effect

The test animals used were 8 week old female mice of the ICR/Jcl strain and were employed in groups of 5 mice for each test. Into each mouse were transplanted intraperitoneally 1×10$^5$ ascites cells of sarcoma 180. The day after transplantation, the test compound, dissolved in sterilized physiological saline, was administered in a single dose (in the amount shown in the following Table 8) intraperitoneally to the animals. A control group was given an intraperitoneal administration of sterilized physiological saline without any active compound.

The results are reported in the following Table 8 as follows:

$T_t/T_c$, where $T_t$ is the mean survival time (in days) of the mice of a test group (i.e. to which one of the test compound was administered) and $T_c$ is the mean survival time (in days) of the control group;

ILS (%), i.e. the increase in lifespan, which is calculated as $(T_t-T_c)$ expressed as a percentage of $T_c$; and number surviving after 60 days, in which the first number is the number of animals surviving, and the second number is the number in the test group.

TABLE 8

| Test Cpd. - Cpd. of Ex. No. | Dose (mg/kg) | $T_t/T_c$ | ILS (%) | No. surviving after 60 days |
|---|---|---|---|---|
| 1 | 5 | 38.6/14.3 | 169 | 2/5 |
| 1 | 10 | 33.8/14.3 | 136 | 1/5 |
| 3 | 10 | 32.6/14.3 | 127 | 1/5 |
| 5 | 5 | 35.2/13.7 | 157 | 2/5 |
| 6 | 20 | 35.0/13.7 | 155 | 0/5 |

The above Table 8 clearly shows that these compounds of the invention, when administered in doses from 5 to 2 mg/kg bodyweight, can prolong the lifespan of the mouse by about 2.5 times that of the untreated mice. In particular, at the end of 60 days, the compounds of Examples 1 and 5 kept 2 of the 5 mice alive, whilst the compound of Example 3 kept 1 mouse of the 5 alive, indicating their significant anti-tumor effect.

EXPERIMENT 2

Hypotensive effect

The hypotensive effect of the compounds of the invention, as well as the known compound C$_{16}$-PAF, were examined by the method of Blank et al. [M. L. Blank et al., Res. Commun. Chem. Pathol. Pharmacol., 38, 3–20 (1982)]. C$_{16}$ PAF has the formula:

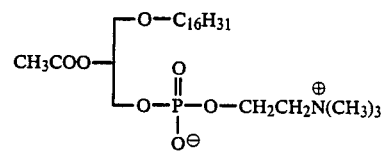

The results are shown in the following Table 9.

EXPERIMENT 3

Platelet aggregating activity

The platelet aggregating activity of the compounds of the invention using rabbits' platelet-rich plasma was examined by the method of Born et al. [Born et al., J. Physiol., 162, 67–68 (1962)]. The EC$_{50}$ values were calculated. As in Experiment 2, C$_{16}$ PAF was used as a reference. The results are also shown in the following Table 9.

TABLE 9

| Test Cpd. - Cpd. of Ex. No. | Hypotensive effect relative potency | Platelet aggregating effect (EC$_{50}$:M) |
|---|---|---|
| 1 | 1:30,000 | >10$^{-4}$ |
| 3 | 1:30,000 | >4 × 10$^{-4}$ |
| 5 | 1:30,000 | >10$^{-4}$ |
| C$_{16}$PAF | 1:1 | 9 × 10$^{-9}$ |

In contrast to C$_{16}$ PAF, which was used as the control, the compounds of the invention, as may be seen from the above Table 9, have essentially no hypotensive or blood platelet aggregating effects, which are considered to be indices of PAF-like activity. This excellent characteristic of the compounds of the invention is believed to be unique amongst anti-tumor compounds of this type.

We claim:

1. A compound of formula (I):

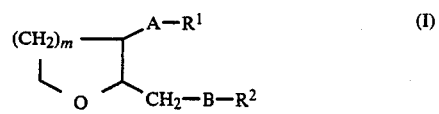

in which
   m is an integer of from 1 to 2;
   A and B are independently selected from the group consisting of oxygen atoms and sulfur atoms; and one of R$^1$ and R$^2$ represents a C$_{10}$–C$_{22}$ alkyl group and the other represents a group of formula (II):

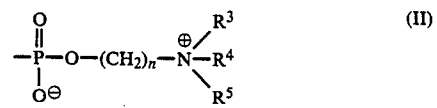

in which:
   n represents an integer of from 2 to 3;
   R$^3$, R$^4$ and R$^5$ are independently selected from the group consisting of hydrogen atoms and C$_1$–C$_6$ alkyl groups, or R$^3$, R$^4$ and R$^5$ together with the nitrogen atom to which they are attached, represent 1-pyridinium, 1-quinolinium, or 2-isoquinolinium; or a pharmaceutically acceptable salt thereof.

2. A compound as claimed in claim 1, wherein A and B both represent oxygen atoms.

3. A compound as claimed in claim 1, wherein n is 2.

4. A compound as claimed in claim 1, wherein $R^3$, $R^4$ and $R^5$ are all $C_1$-$C_6$ alkyl groups, or $R^3$, $R^4$ and $R^5$ together with the nitrogen atom to which they are attached represent a 1-pyridinium.

5. A compound as claimed in claim 1, wherein the groups represented by —A—$R^1$ and —$CH_2$—B—$R^2$ are in the trans configuration.

6. A compound as claimed in claim 1, wherein:
one of $R^1$ and $R^2$ represents an alkyl group having from 16 to 18 carbon atoms;
m is 1 or 2;
A and B both represent oxygen atoms;
n is 2;
$R^3$, $R^4$ and $R^5$ all represent $C_1$-$C_6$ alkyl groups, or $R^3$, $R^4$ and $R^5$ together with the nitrogen atom to which they are attached represent 1-pyridinium
and
the groups represented by —A—$R^1$ and —$CH_2$—B—$R^2$ are in the trans configuration.

7. A compound of formula:

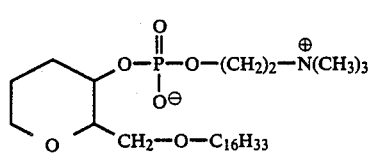

in the trans form; or a pharmaceutically acceptable salt thereof.

8. A compound of formula:

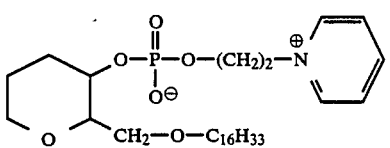

in the trans form; or a pharmaceutically acceptable salt thereof.

9. A compound of formula:

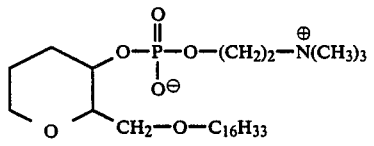

in the cis form; or a pharmaceutically acceptable salt thereof.

10. A compound of formula:

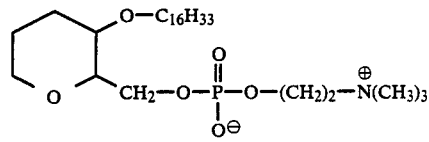

in the trans form; or a pharmaceutically acceptable salt thereof.

11. A compound of formula:

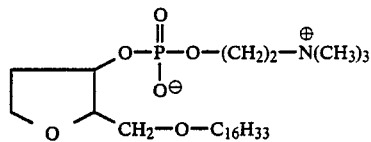

in the trans form; or a pharmaceutically acceptable salt thereof.

12. A compound of formula:

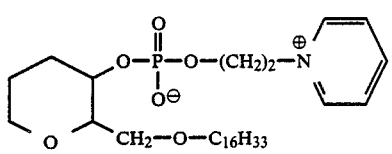

in the cis form; or a pharmaceutically acceptable salt thereof.

13. A compound of formula:

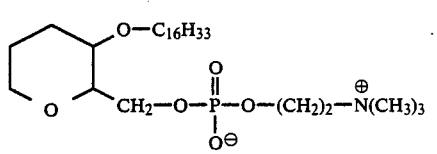

in the cis form; or a pharmaceutically acceptable salt thereof.

14. A compound of formula:

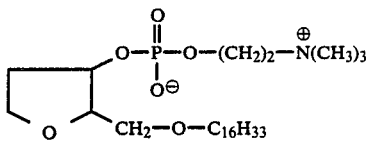

in the cis form; or a pharmaceutically acceptable salt thereof.

* * * * *